United States Patent [19]

Meyer et al.

[11] 4,442,100

[45] Apr. 10, 1984

[54] SUBSTITUTED 2-AMINO-3,4-DIHYDROPYRIDINE DERIVATIVES, THEIR PRODUCTION AND THEIR MEDICINAL USE

[75] Inventors: Horst Meyer; Rüdiger Sitt; Günter Thomas, all of Wuppertal; Benward Garthoff, Hilden; Robertson Towart; Ulrich Rosentreter, both of Wuppertal, all of Fed. Rep. of Germany

[73] Assignee: Bayer Aktiengesellschaft, Leverkusen, Fed. Rep. of Germany

[21] Appl. No.: 210,119

[22] Filed: Nov. 24, 1980

[30] Foreign Application Priority Data

Dec. 11, 1979 [DE] Fed. Rep. of Germany ....... 2949701
May 2, 1980 [DE] Fed. Rep. of Germany ....... 3016874

[51] Int. Cl.$^3$ .................. A61K 31/495; C07D 241/04; C07D 401/04
[52] U.S. Cl. .................................... 424/250; 424/263; 544/238; 544/333; 544/353; 544/357; 544/359; 544/360; 546/144; 546/167; 546/272; 546/280; 546/281; 546/304; 546/311
[58] Field of Search ............... 544/360, 238, 295, 353, 544/357, 359; 424/250

[56] References Cited

U.S. PATENT DOCUMENTS 3,959,292  5/1976  Meyer et al. ..................... 260/326.2
4,136,187  1/1979  Meyer et al. ......................... 424/250

FOREIGN PATENT DOCUMENTS 2239815  2/1974  Fed. Rep. of Germany .

OTHER PUBLICATIONS

Govier, J.; Pharmacol. and Exp. Therapy; 148, (1965), pp. 100–105.
Meyer, et al., Liebigs Ann. Chem., (1977), pp. 1895–1908.
Zimmerman, et al., J. A. C. S., 81, (1959), p. 113.
Rosenblueth, et al., J. Cellular and Comparative Physiology, 33, (1949), pp. 405–439.

Primary Examiner—Joseph Paul Brust
Attorney, Agent, or Firm—Sprung, Horn, Kramer & Woods

[57] ABSTRACT

The invention relates to substituted 2-amino-3,4-dihydropyridine derivative compounds useful, for example as lipid absorption inhibitors.

Also included in the invention are methods for the manufacture of said active compounds, compositions containing them and methods for the use of said compounds and compositions.

14 Claims, No Drawings

SUBSTITUTED 2-AMINO-3,4-DIHYDROPYRIDINE DERIVATIVES, THEIR PRODUCTION AND THEIR MEDICINAL USE

The present invention relates to certain new substituted 2-amino-3,4-dihydropyridine derivatives, to a process for their production and to their use as lipid absorption inhibitors i.e. antilipidemic agents.

It is already known that 3,5-bis-alkoxycarbonyl-2-alkylaminodihydropyridines have circulation-influencing actions, in particular a hypotensive action (see DT-OS (German Published Specification) 2,239,815). A lipid absorption-inhibiting action of dihydropyridines has not hitherto been disclosed.

According to the present invention there are provided compounds which are substituted 2-amino-3,4-dihydropyridine derivatives of the formula (I)

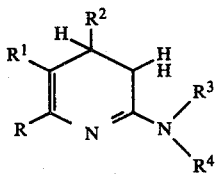

or a salt thereof,
in which
R represents a hydrogen atom or an alkyl radical which is optionally substituted (preferably at the terminal carbon atom) by hydroxyl, halogen, alkoxy or the group

in which
R' and R'' are identical or different and each denote a hydrogen atom or an alkyl or aralkyl radical, or
R represents an optionally substituted aralkyl or aryl (preferably mono- or bi-cyclic carbocyclic aryl) radical which is optionally substituted by 1 or 2 identical or different substituents selected from halogen, alkyl, alkoxy, alkylmercapto and trifluoromethyl,
$R^1$ and $R^2$ are identical or different and each represent an aryl (preferably a mono- or bi-cyclic carbocyclic aryl) radical or a hetero-aryl radical selected from thienyl, furyl, pyrryl, pyrazolyl, imidazolyl, oxazolyl, isoxazolyl, thiazolyl, pyridyl, pyridazinyl, pyrimidyl, pyrazinyl, quinolyl, isoquinolyl, indolyl, benzimidazolyl, quinazolyl and quinoxalyl, the aryl radical and the hetero-aryl radicals optionally containing 1, 2 or 3 identical or different substituents selected from phenyl, alkyl, alkenyl, alkinyl, alkoxy, alkenoxy, alkinoxy, alkylene, oxa alkylene, dioxaalkylene, halogen, trifluoromethyl, trifluoromethoxy, trifluoromethylthio, hydroxyl, amino, alkylamino, dialkylamino, alkyl-arylamino, nitro, cyano, azido, carboxyl, carbalkoxy, carboxamido, sulphonamido or $SO_m$-alkyl (in which m is 0, 1 or 2), and the alkyl and alkoxy substituents in turn being optionally substituted by alkoxy, carboxyl, carbalkoxy, halogen, amino, alkylamino or dialkylamino, and
$R^3$ and $R^4$ are identical or different and each represent a hydrogen atom or an alkyl, aralkyl, alkenyl or alkinyl radical, the alkyl and alkenyl radicals being straight-chain, branched or cyclic and being optionally substituted by the group $COR^5$,
in which
$R^5$ denotes an alkyl, aralkyl or aryl radical or $R^3$ and $R^4$, together with the nitrogen atom to which they are attached, form a 4-membered to 7-membered (preferably 5- to 6-membered) ring which is optionally interrupted by an oxygen, a sulphur, an NH group or an $NR^6$ group,
in which
$R^6$ has a meaning indicated above in the definition of $R^1$ and $R^2$.

According to the present invention there is further provided a process for the production of a compound of the present invention in which an $\alpha,\beta$-unsaturated oxo compound of the formula

in which
R, $R^1$ and $R^2$ have the meaning indicated above, is reacted with a 3,3-diamino-acrylic acid ester of the formula

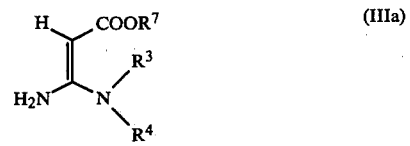

or with its tautomeric imine form of the formula

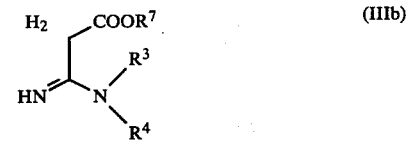

in which
$R^3$ and $R^4$ have the meanings indicated above and
$R^7$ represents an optionally substituted alkyl or aralkyl radical,
in the presence of an inert organic solvent, optionally in the presence of an acid or basic catalyst and optionally at a temperature between 20° and 150° C.

If 3-(p-chlorophenyl)-4-α-pyridyl-but-3-en-2-one and 3-amino-3-$N^4$-(p-trifluoromethylphenyl)-piperazino-acrylic acid ethyl ester are used as starting compounds, the course of the reaction is illustrated by the following equation:

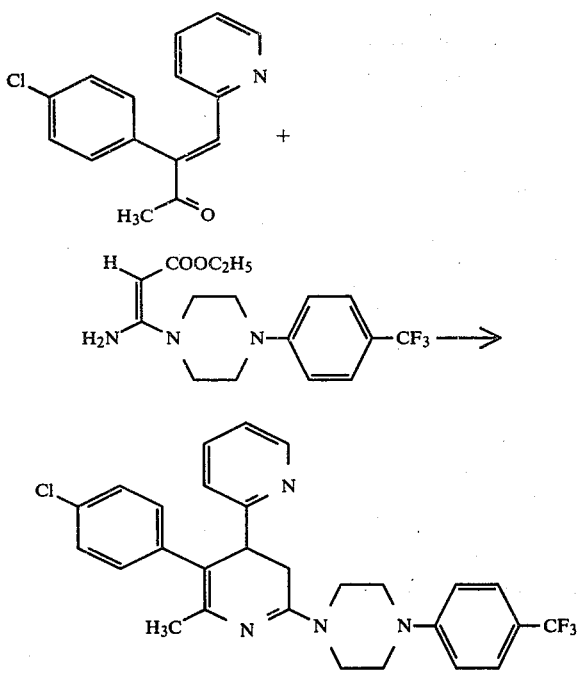

The α,β-unsaturated oxo compounds of the formula (II) which can be used according to the invention are known, or they can be prepared by known methods (see J. Am. Chem. Soc. 81, 113 (1959)).

The 3,3-diaminoacrylic acid esters of the formula (IIIa), and their tautomeric imine forms, which can be used as starting compounds are likewise known, or they can be prepared by known methods (see DT-OS (German Published Specification) 2,239,815 which corresponds to U.S. Pat. Nos. 3,959,292 and 4,136,187, and H. Meyer, F. Bossert and H. Horstmann, Liebigs Ann. Chem. 1977, 1895).

Any inert organic solvent can be used as a diluent in carrying out the process according to the invention. Such solvents include, as preferences, lower alcohols, particularly alkanols having 1 to 3 carbon atoms, (such as methanol, ethanol and propanol), ethers (such as dioxane and diethyl ether), ketones (such as acetone or methyl ethyl ketone), glacial acetic acid, pyridine, dimethylformamide, diethylformamide, dimethylsulphoxide and acetonitrile.

The reaction temperatures can be varied within a substantial range. In general, the reaction is carried out between 20° and 150° C., preferably at 30° to 120° C. and in particular at the boiling point of the solvent.

Preferred acid catalysts which may be mentioned are: mineral acids, such as sulphuric acid or phosphoric acid, and sulphonic acids, such as hydrocarbon sulphonic acid, e.g. toluenesulphonic acid, and preferred basic catalysts which may be mentioned are alkali metal and alkaline earth metal hydroxides and alcoholates (particularly alkanolates), especially alkali metal alcoholates (particularly alkanolates).

The reaction can be carried out under normal pressure, but also under elevated pressure. In general, it is carried out under normal pressure.

The substances participating in the reaction are preferably each employed in equi-molar amounts in carrying out the process.

Unless expressly indicated otherwise herein, "alkyl" in the present application represents straight-chain, branched or cyclic alkyl with up to 10 carbon atoms, in particular straight-chain or branched alkyl with up to 6 carbon atoms; "aryl" preferably denotes mono- or bicyclic carbocyclic aryl, such as phenyl or naphthyl and "aralkyl" preferably represents mono- or by-cyclic carbocyclic aryl-$C_1$-$C_2$-alkyl, such as benzyl, phenethyl or phenylpropyl; "alkoxy" and "alkylmercapto" each represent straight-chain or branched alkoxy alkenoxy, alkinoxy or alkylmercapto with up to 6 carbon atoms and "halogen" preferably denotes fluorine, chlorine or bromine.

Also, unless expressly indicated otherwise herein, "alkenyl" and "alkinyl" as well as "alkenyloxy" and "alkinyloxy" represent moieties having up to 10, preferably up to 6 carbon atoms, "alkylene", "oxaalkylene" and "dioxaalkylene" preferably having 3 to 7 especially 5 to 6 ring members, and "alkylamino", "dialkylamino", "alkyl-aryl amino", "alkylsulphonyl" and "carbalkoxy" each represent moieties wherein "alkyl" and "aryl" are defined as immediately above.

Compounds of the formula (I) which are of particular interest are those
in which
R represents a hydrogen atom, a straight-chain or branched alkyl radical which has up to 6 carbon atoms and is optionally monosubstituted or disubstituted by hydroxyl, alkoxy with 1 to 4 carbon atoms, amino, monoalkylamino, dialkylamino or benzyl-alkylamino, the substituent alkyl groups mentioned containing 1 to 4 carbon atoms, or a phenyl or benzyl radical, the phenyl ring thereof optionally being monosubstituted or disubstituted by identical or different substituents selected from fluorine, chlorine, bromine, trifluoromethyl and alkyl, alkoxy and alkylmercapto with in each case 1 to 4 carbon atoms,
$R^1$ and $R^2$ are identical or different and each represent a phenyl, naphthyl or pyridyl radical, these aromatic rings optionally containing 1 or 2 identical or different substituents selected from nitro, cyano, azido, hydroxyl, amino, carboxyl, halogen, phenyl, alkyl, alkoxy, trifluoromethyl, trifluoromethoxy, trifluoromethylthio, alkylmercapto, alkylsulphonyl and alkylamino, and the alkyl- and alkoxy-group containing radicals mentioned each containing 1 to 4 carbon atoms, and
$R^3$ and $R^4$ are identical or different and each represent a hydrogen atom, a benzyl radical, an alkyl or alkenyl radical with up to 6 carbon atoms, the alkyl and benzyl radicals optionally being substituted by a group $COR^5$,
in which
$R^5$ denotes an alkyl radical with 1 to 4 carbon atoms or a benzyl or phenyl radical, or
$R^3$ and $R^4$, together with the nitrogen atom in which they are attached, form a 5-membered to 7-membered ring which is optionally interrupted by oxygen, sulphur, NH or $NR^6$,
in which
$R^6$ has a meaning indicated immediately above in the definition of $R^1$ and $R^2$.

Compounds of the general formula (I) which are to be singled out in particular are those
in which
R represents a hydrogen atom, an alkyl radical with 1 to 4 carbon atoms or a benzyl or phenyl radical, $R^1$ and $R^2$ are identical or different and each represents a pyridyl or phenyl radical, the phenyl ring optionally carrying 1 or 2 identical or different substituents selected from fluorine, chlorine, nitro, cyano, amino, azido, trifluoromethyl, trifluoromethoxy, trifluoromethylthio, alkylmercapto, or alkyl, each with 1 to 4 carbon atoms, alkoxy with 1 to 4 carbon atoms, phenyl and alkylamino with 1 to 2 carbon atoms in each alkyl radical, and $R^3$ and $R^4$ are identical or different and represent a hydrogen atom, an alkyl radical with 1 to 4 carbon atoms or a benzyl radical, or $R^3$ and $R^4$, together with the nitrogen atom to which they are attached, form a 5-membered or 6-membered ring which is optionally interrupted by a group NH or $NR^6$, in which $R^6$ has a meaning indicated immediately above in the definition of $R^1$ and $R^2$.

Surprisingly, the compounds of the formula (I) according to the invention exhibit a very powerful action in the treatment of disorders in fat metabolism. In particular, they have the effect of lowering the increased level of cholesterol in serum and at the same time reduce hypertriglyceridaemia.

The compounds according to the invention are therefore advantageously suitable for the treatment of hyperlipoproteinaemia, arteriosclerosis and adiposity and for the treatment of metabolic disorders caused by these conditions.

The compounds according to the invention are particularly suitable as lipid absorption inhibitors, diuretic agents, saluretic agents, antiarrythmic agents and cardiotonic agents.

The diuretic and saluretic action is investigated using rats. Male rats which, whilst fasting, receive 10 ml/kg of liquid by a stomach tube are used for this investigation. This liquid contains 0.5% of tylose and a particular dose of the test preparation (control animals receive no test preparation). The urine passed is collected for 6 hours and the sodium content and potassium content is then determined photometrically in the customary manner.

The antiarrythmic action of the compounds according to the invention is demonstrated by the effects on the rest period of the cardiac muscle by means of standard test processes. As is known, therapeutic doses of antiarrythmic agents prolong the rest period of the cardiac muscle. This prolonging of the rest period and the determination of the contracting force on isolated prepared sections of cardiac muscle are effected by known methods (see: Govier, J. Pharmacol. Exp. Ther. 148, 100–105, (1965) and Roseblueth at al., J. Cell Comp. Physiol. 33, 405–439 (1949)).

None of these actions have hitherto been disclosed for the dihydropyridine class of substances. It is thus to be described as decidedly surprising that the compounds according to the invention have these new and advantageous actions. As a novel class of substances for the treatment of disorders in metabolism and disorders in cardiac rythm whilst at the same time being well tolerated, they are an enrichment of pharmacy.

As stated above, the invention also relates to the use in medicine of the compounds of the invention.

The present invention provides a pharmaceutical composition containing as active ingredient a compound of the invention in admixture with an inert pharmaceutical carrier, such as a solid or liquefied gaseous diluent, or in admixture with a liquid diluent other than a solvent of a molecular weight less than 200 (preferably less than 350) except in the presence of a surface active agent.

The invention further provides a pharmaceutical composition containing as active ingredient a compound of the invention in the form of a sterile and/or physiologically isotonic aqueous solution.

The invention also provides a medicament in dosage unit form comprising a compound of the invention.

The invention also provides a medicament in the form of tablets (including lozenges and granules), dragees, capsules, pills, ampoules or suppositories comprising a compound of the invention.

"Medicament" as used in this Specification means physically discrete coherent portions suitable for medical administration. "Medicament in dosage unit form" as used in this Specification means physically discrete coherent units suitable for medical administration each containing a daily dose or a multiple (up to four times) or submultiple (down to a fortieth) of a daily dose of the compound of the invention in association with a carrier and/or enclosed within an envelope. Whether the medicament contains a daily dose or, for example, a half, a third or a quarter of a daily dose will depend on whether the medicament is to be administered once, or for example, twice, three times or four times a day respectively.

The pharmaceutical composition according to the invention may, for example, take the form of suspensions, solutions and emulsions of the active ingredient in aqueous or non-aqueous diluents or syrups.

The diluents to be used in pharmaceutical compositions (e.g. granulates) adapted to be formed into tablets, dragees, capsules and pills include the following: (a) fillers and extenders, e.g. starch, sugars, mannitol, and silicic acid; (b) binding agents, e.g. carboxymethyl cellulose and other cellulose derivatives, alginates, gelatine and polyvinyl pyrrolidone; (c) moisturizing agents, e.g. glycerol; (d) disintegrating agents, e.g. agar-agar, calcium carbonate and sodium bicarbonates; (e) agents for retarding dissolution e.g. paraffin; (f) resorption accelerators, e.g. quaternary ammonium compounds; (g) surface active agents, e.g. cetyl alcohol, glycerol monostearate; (h) adsorptive carriers, e.g. kaolin and bentonite; (i) lubricants, e.g. talc, calcium and magnesium stearate and solid polyethylene glycols.

The tablets, dragees, capsules and pills formed from the pharmaceutical compositions of the invention can have the customary coatings, envelopes and protective matrices, which may contain opacifiers. They can be so constituted that they release the active ingredient only or preferably in a particular part of the intestinal tract, possibly over a period of time. The coatings, envelopes and protective matrices may be made, for example, of polymeric substances or waxes.

The ingredient can also be made up in microencapsulated form together with one or several of the above-mentioned diluents.

The diluents to be used in pharmaceutical compositions adapted to be formed into suppositories can, for example, be the usual water-soluble diluents, such as polyethylene glycols and fats (e.g. cocoa oil and high esters (e.g. $C_{14}$-alcohol with $C_{16}$-fatty acid)) or mixtures of these diluents.

The pharmaceutical compositions which are solutions and emulsions can, for example, contain the customary inert pharmaceutical carrier, e.g. diluents (with, of course, the above-mentioned exclusion of solvents having a molecular weight below 200 except in the presence of a surface-active agent), such as solvents, dissolving agents and emulsifiers; specific examples of such diluents are water, ethyl alcohol, isopropyl alcohol, ethyl carbonate, ethyl acetate, benzyl alcohol, benzyl benzoate, propylene glycol, 1,3-butylene glycol, dimethylformamide, oils (for example ground nut oil), glycerol tetrahydrofurfuryl alcohol, polyethylene glycols and fatty acid esters of sorbitol or mixtures thereof.

For parenteral administration, solutions and emulsions should be sterile, and, if appropriate, blood-isotonic.

The pharmaceutical compositions which are suspensions can contain the usual diluents, such as liquid diluents, e.g. water, ethyl alcohol, propylene glycol, surface-active agents (e.g. ethoxylated isostearyl alcohols, polyoxyethylene sorbite and sorbitane esters), microcrystalline cellulose, aluminium metahydroxide, bentonite, agar-agar and tragacanth or mixtures thereof.

All the pharmaceutical compositions according to the invention can also contain colouring agents and preservatives as well as perfumes and flavouring additions (e.g. peppermint oil and eucalyptus oil) and sweetening agents (e.g. saccharin).

The pharmaceutical compositions according to the invention generally contain from 0.1 to 99.5% usually from 0.5 to 95% of the active ingredient by weight of the total composition.

In addition to a compound of the invention, the pharmaceutical compositions and medicaments according to the invention can also contain other pharmaceutically active compounds. They may also contain a plurality of compounds of the invention.

Any diluent in the medicaments of the present invention may be any of those mentioned above in relation to the pharmaceutical compositions of the present invention. Such medicaments may include solvents of molecular weight less than 200 as sole diluent.

The discrete coherent portions constituting the medicament according to the invention will generally be adapted by virtue of their shape or packaging for medical administration and may be, for example, any of the following: tablets (including lozenges and granulates), pills, dragees, capsules, suppositories and ampoules. Some of these forms may be made up for delayed release of the active ingredient. Some, such as capsules, include a protective envelope which renders the portions of the medicament physically discrete and coherent.

The preferred daily dose for administration of the medicaments of the invention is 250 to 5000 mg of active ingredient.

The product of the above-mentioned pharmaceutical compositions and medicaments is carried out by any method known in the art, for example, by mixing the active ingredient(s) with the diluent(s) to form a pharmaceutical composition (e.g. a granulate) and then forming the composition into the medicament (e.g. tablets).

This invention further provides a method of combating the above-mentioned diseases in warm-blooded animals, which comprises administering to the animals a compound of the invention alone or in admixture with an inert pharmaceutical carrier, e.g. a diluent or in the form of a medicament according to the invention.

It is envisaged that these active compounds will be administered perorally, parenterally (for example intramuscularly, intraperitoneally, subcutaneously and intravenously) or rectally preferably orally. Preferred pharmaceutical compositions and medicaments are therefore those adapted for administration such as oral administration. Administration in the method of the invention is preferably oral administration.

In general it has proved advantageous to administer amounts of from 1.0 mg to 500 mg/kg, preferably 5 mg to 100 mg/kg of body weight per day, and in particular before or/and during or/and after meals, to achieve effective results. A single administration preferably contains the active compound or compounds in amounts of 1 to 100 mg/kg of body weight. Nevertheless, it can at times be necessary to deviate from those dosage rates, and in particular to do so as a function of the nature and body weight of the human or animal subject to be treated, the individual reaction of this subject to the treatment, the type of formulation in which the active ingredient is administered and the mode in which the administration is carried out, and the point in the progress of the disease or interval at which it is to be administered. Thus it may in some case suffice to use less than the above-mentioned minimum dosage rate, whilst other cases the upper limit mentioned must be exceeded to achieve the desired results. Where larger amounts are administered it can be advisable to divide these into several individual administrations over the course of day.

The following Examples illustrate processes for the production of compounds of the present invention.

EXAMPLE 1

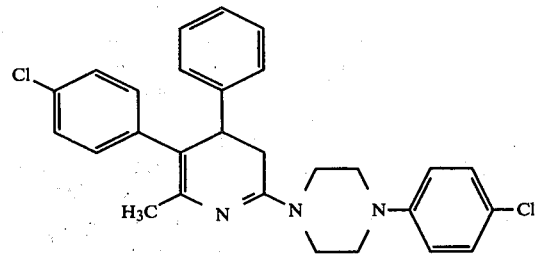

0.033 mole of 3-(p-chlorophenyl)-4-phenyl-but-3-en-2-one and 0.033 mole of 3-amino-3-N⁴-(p-chlorophenyl)-piperazinoacrylic acid ethyl ester in 100 ml of ethanol are whirled under reflux for 30 hours. After cooling the reaction mixture, the precipitate which has separated out is filtered off and washed with ethanol. After recrystallisation from ethanol, 5-(4-chlorophenyl)-2-(4-chlorophenylpiperazino)-6-methyl-4-phenyl-3,4-dihydropyridine of melting point 161°-162° C. is obtained. Yield: 48% of theory.

In the Examples in the following table, the compounds are prepared analogously to Example 1:

TABLE 1

| Example No. | R | R₁ | R₂ | R₃ R₄ | Recrystallised from the solvent | Melting point: °C. | Yield % of theory |
|---|---|---|---|---|---|---|---|
| 2 | $CH_3$ | Ph- | Ph- | $(-C_2H_4)_2N$-Ph | Ethanol | 103–104 | 17 |
| 3 | $CH_3$ | Ph- | $H_3C$-C₆H₄- | $(-C_2H_4)_2N$-Ph | Ethanol | 142–144 | 16 |
| 4 | $CH_3$ | Ph- | 2-$CH_3$-C₆H₄- | $(-C_2H_4)_2N$-Ph | Ether | 124–126 | 25 |
| 5 | $CH_3$ | Ph- | 2-Cl-C₆H₄- | $(-C_2H_4)_2N$-Ph | Ethanol | 101–105 | 48 |
| 6 | $CH_3$ | $H_3CO$-C₆H₄- | Ph- | $(-C_2H_4)_2N$-Ph | Ethanol | 132–134 | 16 |
| 7 | $CH_3$ | Ph- | Ph- | $(-C_2H_4)_2N$-C₆H₄-$C_2H_5$ | Ethanol | 97–98 | 21 |
| 8 | $CH_3$ | Ph- | Ph- | $(-C_2H_4)_2N$-C₆H₄-Cl | Ethanol | 106–108 | 13 |
| 9 | $CH_3$ | Cl-C₆H₄- | Ph- | $(-C_2H_4)_2N$-Ph | Dioxane | 180–181 | 69 |
| 10 | $CH_3$ | $H_3C$-C₆H₄- | Ph- | $(-C_2H_4)_2N$-Ph | Ethanol | 130–132 | 40 |
| 11 | $CH_3$ | Cl-C₆H₄- | Ph- | $(-C_2H_4)_2N$-C₆H₄-F | Ethanol | 155–157 | 43 |
| 12 | $CH_3$ | Ph- | 2-Cl-C₆H₄- | $(-C_2H_4)_2N$-C₆H₄-$C_2H_5$ | Ethanol | 122–124 | 43 |
| 13 | $CH_3$ | Ph- | 2-Cl-C₆H₄- | $(-C_2H_4)_2N$-C₆H₄-Cl | Ethanol | 124–131 | 45 |
| 14 | $CH_3$ | Ph- | 2-Cl-C₆H₄- | $(-C_2H_4)_2N$-C₆H₄-$CH_3$ | Ethanol | 120–121 | 57 |
| 15 | $CH_3$ | $H_3C$-C₆H₄- | Ph- | $(-C_2H_4)_2N$-C₆H₄-Cl | Ethanol | 137–138 | 37 |
| 16 | $CH_3$ | $H_3CO$-C₆H₄- | Ph- | $(-C_2H_4)_2N$-C₆H₄-Cl | Ethanol | 137–138 | 39 |
| 17 | $CH_3$ | Ph- | Ph- | $(-C_2H_4)_2N$-C₆H₄-$C_4H_{9n}$ | Methanol × 2HCl | 223–224 | 23 |

TABLE 1-continued

Structure:
- Pyridine-type ring with R at position 6, R$_1$ at position 5, R$_2$ at position 4, and N(R$_3$)(R$_4$) at position 2.

| Example No. | R | R$_1$ | R$_2$ | R$_3$ R$_4$ | Recrystallised from the solvent | Melting point: °C | Yield % of theory |
|---|---|---|---|---|---|---|---|
| 18 | CH$_3$ | 4-CH$_3$-C$_6$H$_4$- | C$_6$H$_5$- | (—C$_2$H$_4$)$_2$N—C$_6$H$_4$—CH$_3$ | Ethanol | 100–102 | 35 |
| 19 | CH$_3$ | 4-H$_3$CO-C$_6$H$_4$- | C$_6$H$_5$- | (—C$_2$H$_4$)$_2$N—C$_6$H$_4$—F | Ethanol | 118–119 | 43 |
| 20 | CH$_3$ | C$_6$H$_5$- | 3-Cl-C$_6$H$_4$- | (—C$_2$H$_4$)$_2$N—C$_6$H$_4$—OCH$_3$ | Ethanol | 112 | 38 |
| 21 | CH$_3$ | 4-Cl-C$_6$H$_4$- | 3-Cl-C$_6$H$_4$- | (—C$_2$H$_4$)$_2$N—C$_6$H$_5$ | Ethanol | 114 | 65 |
| 22 | CH$_3$ | C$_6$H$_5$- | C$_6$H$_5$- | (—C$_2$H$_4$)$_2$N—C$_6$H$_4$—F | Methanol × 2HCl | 242–243 | 21 |
| 23 | CH$_3$ | 4-CH$_3$-C$_6$H$_4$- | C$_6$H$_5$- | (—C$_2$H$_4$)$_2$N—C$_6$H$_4$—F | Ethanol | 104–105 | 31 |
| 24 | CH$_3$ | C$_6$H$_5$- | 4-CH$_3$-C$_6$H$_4$- | (—C$_2$H$_4$)$_2$N—C$_6$H$_4$—OCH$_3$ | Ethanol | 138 | 48 |
| 25 | CH$_3$ | 4-Cl-C$_6$H$_4$- | 3-Cl-C$_6$H$_4$- | (—C$_2$H$_4$)$_2$N—C$_6$H$_4$—C$_2$H$_5$ | Ethanol | 98 | 54 |
| 26 | CH$_3$ | 4-Cl-C$_6$H$_4$- | 4-Cl-C$_6$H$_4$- | (—C$_2$H$_4$)$_2$N—C$_6$H$_5$ | Ethanol | 140 | 38 |
| 27 | CH$_3$ | 4-H$_3$CO-C$_6$H$_4$- | C$_6$H$_5$- | (—C$_2$H$_4$)$_2$N—C$_6$H$_4$—OCH$_3$ | Ethanol | 122 | 49 |
| 28 | CH$_3$ | 4-H$_3$CO-C$_6$H$_4$- | C$_6$H$_5$- | (—C$_2$H$_4$)$_2$N—C$_6$H$_4$—C$_2$H$_5$ | Ethanol | 94 | 33 |
| 29 | CH$_3$ | C$_6$H$_5$- | 3-H$_3$CO-C$_6$H$_4$- | (—C$_2$H$_4$)$_2$N—C$_6$H$_5$ | Methanol × 2HCl | 139 | 25 |
| 30 | CH$_3$ | 4-Cl-C$_6$H$_4$- | C$_6$H$_5$- | (—C$_2$H$_4$)$_2$N—C$_6$H$_4$—C$_4$H$_9$ | Ethanol | 48 | 24 |
| 31 | CH$_3$ | C$_6$H$_5$- | C$_6$H$_5$- | H   H | Cyclohexan | 164 | 19 |
| 32 | CH$_3$ | C$_6$H$_5$- | C$_6$H$_5$- | —(CH$_2$)$_4$— | Ether | 116 | 52 |

TABLE 1-continued

Structure:
$R_1$, $R_2$ on dihydropyridine ring with $R$ at position adjacent to N, and $NR_3R_4$ on the other side.

| Example No. | R | $R_1$ | $R_2$ | $R_3$ | $R_4$ | Recrystallised from the solvent | Melting point: °C. | Yield % of theory |
|---|---|---|---|---|---|---|---|---|
| 33 | CH₃ | phenyl | 2-chlorophenyl | —(CH₂)₄— | | Ethanol | 144 | 57 |
| 34 | CH₃ | phenyl | 2-thienyl | (—C₂H₄)₂N—phenyl | | Ether | 143 | 33 |
| 35 | CH₃ | phenyl | 2-furyl | (—C₂H₄)₂N—phenyl | | Ethanol | 125 | 40 |
| 36 | CH₃ | 4-OCH₃-phenyl | phenyl | —(CH₂)₄— | | Isopropanol | 139 | 53 |
| 37 | CH₃ | 4-Cl-phenyl | phenyl | —(CH₂)₄— | | Isopropanol | 152 | 52 |
| 38 | CH₃ | phenyl | 4-SCF₃-phenyl | (—C₂H₄)₂N—phenyl | | Methanol/Acetone × 2HCl | 225–7 | 33 |
| 39 | CH₃ | 4-OCH₃-phenyl | phenyl | (—C₂H₄)₂N—phenyl | | Ethanol | 132–4 | 15 |
| 40 | CH₃ | phenyl | phenyl | (—C₂H₄)₂N—(2-SCH₃-phenyl) | | Methanol/Acetone × 2HCl | 202–4 | |
| 41 | CH₃ | 4-Cl-phenyl | phenyl | (—C₂H₄)₂N—(4-Cl-phenyl) | | Ethanol | 161–3 | 45 |
| 42 | CH₃ | phenyl | 3-Cl-phenyl | (—C₂H₄)₂N—(4-F-phenyl) | | Methanol/Acetone × 2HCl | 202–5 | 35 |
| 43 | CH₃ | phenyl | 2-Cl-phenyl | (—C₂H₄)₂N—(4-F-phenyl) | | Methanol/Acetone × 2HCl | 202–10z | 20 |
| 44 | CH₃ | 4-Cl-phenyl | phenyl | (—C₂H₄)₂N—(4-C₂H₅-phenyl) | | Methanol/Acetone × 2HCl | 243–4 | 39 |
| 45 | CH₃ | phenyl | 4-CH₃-phenyl | (—C₂H₄)₂N—(4-CH₃-phenyl) | | Methanol/Acetone × 2HCl | 225–7 | 38 |
| 46 | CH₃ | phenyl | 2-Cl-phenyl | (—C₂H₄)₂N—phenyl | | Methanol/Acetone × 2HCl | 221–3 | 18 |

TABLE 1-continued

Structure:

$$\text{R}_1\text{-C(R)=N-C(NR}_3\text{R}_4\text{)-CH}_2\text{-CH(R}_2\text{)-}$$ (dihydropyridine shown in header)

| Example No. | R | R₁ | R₂ | R₃ | R₄ | Recrystallised from the solvent | Melting point: °C. | Yield % of theory |
|---|---|---|---|---|---|---|---|---|
| 47 | CH₃ | phenyl | 3-Cl-phenyl | (—C₂H₄)₂N— | 4-C₄H₉-phenyl | Methanol/Ether × 2HCl | 225–7 | 37 |
| 48 | CH₃ | phenyl | 2-Cl-phenyl | (—C₂H₄)₂N— | 4-OCH₃-phenyl | Methanol/Ether × 2HCl | 221–3 | 17 |
| 49 | CH₃ | phenyl | 2-CF₃-phenyl | (—C₂H₄)₂N— | phenyl | Methanol/Ether × 2HCl | 173–6 | 14 |
| 50 | CH₃ | phenyl | 3-CF₃-phenyl | (—C₂H₄)₂N— | phenyl | Methanol/Ether × 2HCl | 234–6 | 47 |
| 51 | CH₃ | phenyl | 5-methylfuran-2-yl | (—C₂H₄)₂N— | 4-C₂H₅-phenyl | Methanol/Ether × 2HCl | 233–5 | 36 |
| 52 | CH₃ | 4-CH₃-phenyl | 4-CH₃-phenyl | (—C₂H₄)₂N— | phenyl | Cyclohexane | 126–131 | 15 |
| 53 | CH₃ | 4-OCH₃-phenyl | 4-OCH₃-phenyl | (—C₂H₄)₂N— | phenyl | Ethanol | 148 | 17 |
| 54 | CH₃ | 4-F-phenyl | 4-F-phenyl | (—C₂H₄)₂N— | phenyl | Ethanol | 146–148 | 47 |
| 55 | CH₃ | 4-SCH₃-phenyl | 4-SCH₃-phenyl | (—C₂H₄)₂N— | phenyl | Ethanol | 149–151 | 37 |
| 56 | CH₃ | phenyl | 3-CN-phenyl | (—C₂H₄)₂N— | phenyl | Petrolether | 58–63 | 70 |
| 57 | CH₃ | 2-N(CH₃)₂-phenyl | 4-Cl-phenyl | (—C₂H₄)₂N— | phenyl | Ethanol | 190 | 40 |
| 58 | CH₃ | 4-CH₃-phenyl | 4-CH₃-phenyl | —(CH₂)₄— | | Cyclohexane | 99 | 58 |
| 59 | CH₃ | 2-OCH₃-phenyl | 4-OCH₃-phenyl | —(CH₂)₄— | | Ether | 143 | 54 |
| 60 | CH₃ | 2-Cl-phenyl | 4-Cl-phenyl | —(CH₂)₄— | | Cyclohexane | 137 | 47 |
| 61 | CH₃ | 4-OCH₃-phenyl | cyclohexyl | —(CH₂)₄— | | Isopropanol | 139–40 | 53 |

TABLE 1-continued

| Example No. | R | R$_1$ | R$_2$ | R$_3$ R$_4$ | Recrystallised from the solvent | Melting point: °C. | Yield % of theory |
|---|---|---|---|---|---|---|---|
| 62 | CH$_3$ | –C$_6$H$_4$–Cl | –C$_6$H$_5$ | –(CH$_2$)$_4$– | Isopropanol | 152–4 | 52 |
| 63 | CH$_3$ | –C$_6$H$_5$ | furyl (O-ring) | (–C$_2$H$_4$)$_2$N–C$_6$H$_4$–C$_4$H$_9$ | Methanol/Acetone × 2HCl | 224–6 | 44 |
| 64 | CH$_3$ | –C$_6$H$_4$–SCH$_3$ | –C$_6$H$_4$–Cl | (–C$_2$H$_4$)$_2$N–C$_6$H$_5$ | Ethanol | 164 | 37 |
| 65 | CH$_3$ | –C$_6$H$_4$–F | –C$_6$H$_4$–F | –(CH$_2$)$_4$– | Ethanol × HCl | 70 | 46 |
| 66 | CH$_3$ | –C$_6$H$_5$ | –C$_6$H$_4$–OCH$_3$ | (–C$_2$H$_4$)$_2$N–C$_6$H$_4$–OCH$_3$ | Methanol/Acetone | 72–76 | 28 |
| 67 | CH$_3$ | –C$_6$H$_4$–Cl | –C$_6$H$_4$–Br | (–C$_2$H$_4$)$_2$N–C$_6$H$_5$ | Ethanol | 149 | 28 |
| 68 | CH$_3$ | –C$_6$H$_4$–SCH$_3$ | –C$_6$H$_4$–Cl | –(CH$_2$)$_4$– | Cyclohexane/Ether | 142–145 | 62 |
| 69 | CH$_2$CH$_3$ | –C$_6$H$_4$–Cl | –C$_6$H$_4$–Cl | –(CH$_2$)$_4$– | Cyclohexane | 114 | 39 |
| 70 | CH$_2$CH$_3$ | –C$_6$H$_4$–Cl | –C$_6$H$_4$–Cl | (–C$_2$H$_4$)$_2$N–C$_6$H$_5$ | Ethanol/Ether × 2HCl | 240 | 33 |
| 71 | CH$_3$ | –C$_6$H$_4$–Cl | –C$_6$H$_4$–Cl | (–C$_2$H$_4$)$_2$N–C$_6$H$_4$–CF$_3$ | Ethanol | 214 | 25 |
| 72 | CH$_3$ | –C$_6$H$_4$–SCH$_3$ | –C$_6$H$_4$–SCF$_3$ | (–C$_2$H$_4$)$_2$N–C$_6$H$_5$ | Ethanol/Ether × 2HCl | 218 | 11 |
| 73 | CH$_3$ | –C$_6$H$_5$ | –C$_6$H$_4$–CF$_3$ | (–C$_2$H$_4$)$_2$N–C$_6$H$_5$ | Cyclohexane | 118–122 | 14 |
| 74 | CH$_3$ | –C$_6$H$_5$ | –C$_6$H$_4$–Br | (C$_2$H$_4$)$_2$–N–C$_6$H$_5$ | Petroleum ether/diethyl ether | 110 | 23 |
| 75 | CH$_3$ | –C$_6$H$_5$ | –C$_6$H$_4$–Br | –(CH$_2$)$_4$– | diethyl ether Cyclohexane | 86 | 30 |
| 76 | CH$_3$ | –C$_6$H$_5$ | –C$_6$H$_3$–Cl,Cl | (C$_2$H$_4$)–N–C$_6$H$_5$ | Ethanol | 145–150 (decomposition) | 31 |
| 77 | CH$_3$ | –C$_6$H$_5$ | –C$_6$H$_3$–OCH$_3$,OCH$_3$ | (C$_2$H$_4$)–N–C$_6$H$_5$ | Ethanol | 125 | 27 |

TABLE 1-continued

| Example No. | R | R₁ | R₂ | R₃ | R₄ | Recrystallised from the solvent | Melting point: °C. | Yield % of theory |
|---|---|---|---|---|---|---|---|---|
| 78 | CH₃ | —⟨phenyl⟩ | —⟨phenyl, Br, OCH₃⟩ | (C₂H₄)—N | —⟨phenyl⟩ | Petrolether | 65–70 | 40 (amorphous) |
| 79 | —⟨phenyl⟩—Cl | H | —⟨phenyl⟩—Cl | (C₂H₄)₂—N | —⟨phenyl⟩ | | | |

Among the new 2-amino-3,4-dihydropyridine derivative salts of the invention, those salts that are pharmaceutically acceptable, especially such acid-addition salts are particularly important and are preferred.

The new free 2-amino-3,4-dihydropyridine derivatives of the formula (I) and their salts can be interconverted in any suitable manner; methods for such interconversion are known in the art.

Thus, a resulting basic compound can be converted into a corresponding acid addition salts, for example by reacting it with an inorganic or organic acid, such as therapeutically useful acid, or with a corresponding anion exchange preparation, and isolating the desired salt. An acid addition salt may be converted into the free compound by treatment with a base, e.g. a metal hydroxide, ammonia or a hydroxyl ion exchange preparation. Therapeutically useful acids are, for example, inorganic acids, e.g. hydrochloric, hydrobromic, sulfuric, phosphoric, nitric or perchloric acid, or organic acids, e.g. carboxylic or sulfonic acids, such as formic, acetic, propionic, succinic, glycollic, lactic, malic, tartaric, citric, ascorbic, maleic, hydroxymaleic, pyroracemic, phenylacetic, benzoic, 4-aminobenzoic, anthranilic, 4-hydroxybenzoic, salicyclic, aminosalicyclic, embonic, nicotinic, methanesulfonic, ethanesulfonic, hydroxy-ethanesulfonic, ethylenesulfonic, benzenesulfonic, halogenobenzenesulfonic, toluenesulfonic, naphthalenesulfonic and sulfanilic acid; methionine, tryptophan, lysine and arginine.

Salts of the above-mentioned acids or other salts, for example, the picrates, can also be used for purification of the bases obtained; the bases are converted into salts, the salts are separated and the bases are liberated from the salts. In view of the close relationship between the free compounds and the compounds in the form of their salts, whenever a compound is referred to in this context, a corresponding salt is also intended, provided such is possible or appropriate under the circumstances.

The present invention also comprises pharmaceutically acceptable bioprecursors of the active compounds of the present invention.

For the purposes of this specification the term 'pharmaceutically acceptable bioprecursor' of an active compound of the invention means a compound having a structural formula different from the active compound but which nonetheless, upon administration to an animal is converted in the patient's body to the active compound.

What is claimed is:

1. A compound of the formula

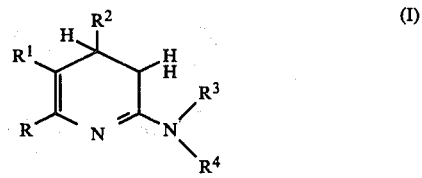

in which R represents a hydrogen atom, a straight-chain or branched alkyl radical which has up to 6 carbon atoms and is optionally mono-substituted or di-substituted by alkoxy with 1 to 4 carbon atoms, dialkylamino with 1 to 4 carbon atoms in each alkyl group, or a phenyl or benzyl radical, the phenyl ring thereof optionally being mono-substituted or di-substituted by identical or different substituents selected from fluorine, chlorine, bromine and alkyl and alkoxy with in each case 1 to 4 carbon atoms, $R^1$ and $R^2$ are identical or different and each represent a phenylnaphthyl or pyridyl radical, these aromatic rings optionally containing 1 or 2 identical or different substituents selected from cyano, hydroxyl, carboxyl, halogen, phenyl, alkyl, alkoxy, trifluoromethyl, trifluoromethoxy, trifluoromethylthio, alkylmercapto, alkylsulphonyl and alkylamino, and the alkyl and alkoxy radicals mentioned each containing 1 to 4 carbon atoms, and $R^3$ and $R^4$ together with a nitrogen atom to which they are attached, form a piperazino ring, which is optionally substituted at the 4-nitrogen atom by an $R^6$ group in which $R^6$ has a meaning indicated above in the definition of $R^1$ and $R^2$.

2. A compound according to claim 1 in which the identical or different substituent(s) on the phenyl, naphthyl or pyridyl radical of $R^1$ and $R^2$ are selected from those listed in claim 1, with the exception of trifluoromethylthio.

3. A pharmaceutical composition containing as an active ingredient an antilipidemically effective amount of a compound according to claim 1, in admixture with an inert pharmaceutical carrier.

4. A pharmaceutical composition of claim 3 in the form of a sterile or physiologically isotonic aqueous solution.

5. A composition according to claim 3 or 4 containing from 0.5 to 95% by weight of the said active ingredient.

6. A medicament in dosage unit form comprising an antilipidemically effective amount of a compound according to claim 1 together with an inert pharmaceutical carrier.

7. A medicament of claim 6 in the form of tablets, pills, dragees, capsules, ampoules, or suppositories.

8. A method of combating lipidemia in warm-blooded animals which comprises administering to the animals an antilipidemically effective amount of an active compound according to claim 1.

9. A method according to claim 8 in which the active compound is administered in an amount of 5 to 100 mg per kg body weight per day.

10. A method according to claim 8 or 9 in which the active compound is administered orally.

11. A compound according to claim 1 in which

R represents an alkyl radical with 1 to 4 carbon atoms or a benzyl or phenyl radical, $R^1$ and $R^2$ are identical or different and each represents a phenyl radical optionally carrying 1 or 2 identical or different substituents selected from fluorine, chlorine, cyano, trifluoromethyl, trifluoromethoxy, trifluoromethylthio, alkylmercapto with 1 to 4 carbon atoms in the above mentioned alkyl radical, phenyl and alkyl amino with 1 to 2 carbon atoms in each alkyl radical, and $R^3$ and $R^4$ together with a nitrogen atom to which they are attached, form a piperazino ring, which is optionally substituted at the 4-nitrogen atom by an $R^6$ group in which $R^6$ has the meaning mentioned in the definition of $R^1$ and $R^2$.

12. A compound according to claim 11 in which the identical or different substituent(s) on the phenyl ring of $R^1$ and/or $R^2$, when representing a phenyl radical, are selected from those listed in claim 11, with the exception of trifluoromethylthio.

13. A compound which is a substituted 2-amino-3,4-dihydropyridine derivative of the formula

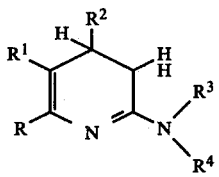

(I)

or a therapeutically useful acid-addition salt thereof, in which

R represents a hydrogen atom or an $C_1$–$C_{10}$ alkyl radical which is optionally substituted by hydroxyl, halogen, $C_1$–$C_6$-alkoxy or the group

in which

R' and R" are identical or different and each denote a hydrogen atom or an $C_1$–$C_{10}$-alkyl or a mono- or bi-cyclic carbocyclic aryl-$C_1$–$C_2$-alkyl radical, or R represents a mono- or bi-cyclic carbocyclic aryl-$C_1$–$C_2$-alkyl aralkyl, or a mono- or bi-cyclic carbocyclic aryl radical which is optionally substituted by 1 or 2 identical or different substituents selected from halogen, $C_1$–$C_{10}$-alkyl, $C_1$–$C_6$-alkoxy, $C_1$–$C_6$-alkylmercapto and trifluoromethyl, $R^1$ and $R^2$ are identical or different and each represent a mono- or bi-cyclic carbocyclic aryl radical or a hetero-atom radical selected from thienyl, furyl, pyrryl, pyrazolyl, imidazolyl, oxazolyl, isoxazolyl, thiazolyl, pyridyl, pyrazinyl, quinolyl, isoquinolyl, indolyl and benzimidazolyl, the aryl radical and the hetero-aryl radicals optionally containing 1, 2 or 3 identical or different substituents selected from phenyl, $C_1$–$C_{10}$ alkyl, $C_2$–$C_{10}$ alkenyl, $C_2$–$C_{10}$ alkinyl, $C_1$–$C_6$ alkoxy, $C_2$–$C_6$ alkenoxy, $C_2$–$C_6$ alkinoxy, $C_3$–$C_7$ alkylene, $C_3$–$C_7$ dioxyalkylene, halogen, trifluoromethyl, trifluoromethoxy, trifluoromethylthio, hydroxyl, amino, $C_1$–$C_{10}$ alkylamino, $C_1$–$C_{10}$ dialkylamino, $C_1$–$C_{10}$ alkyl-a mono- or bicyclic carboxyclic arylamino, nitro, cyano, azido, carboxyl, carb-$C_1$–$C_6$-alkoxy, carboxamido, sulphonamido or $SO_m$-$C_1$–$C_{10}$-alkyl (in which m is 0, 1 or 2, and the alkyl and alkoxy substituents in turn being optionally substituted by $C_1$–$C_6$ alkoxy, carboxyl, carb-$C_1$–$C_6$-alkoxy, halogen, amino, $C_1$–$C_{10}$ alkylamino or $C_1$–$C_6$ dialkylamino, and $R^3$ and $R^4$ together with the nitrogen atom to which they are attached, form a piperazino ring which is optionally substituted at the 4-nitrogen atom by an $R^6$ group which has a meaning indicated above in the definition of $R^1$ and $R^2$.

14. A compound of claim 13 having the formula

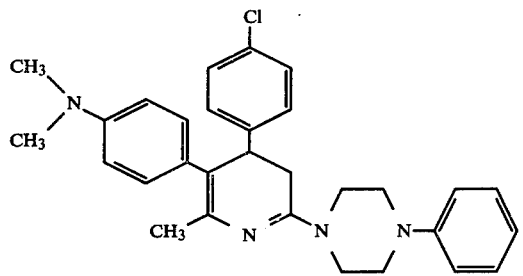

* * * * *

UNITED STATES PATENT AND TRADEMARK OFFICE
CERTIFICATE OF CORRECTION

PATENT NO. : 4,442,100

DATED : April 10, 1984

INVENTOR(S) : Horst Meyer et al

It is certified that error appears in the above-identified patent and that said Letters Patent is hereby corrected as shown below:

Col. 14, last column of Example 40     Insert --41--

Col. 15, Example 61, 3rd column     Delete " " and substitute

Col. 19, line 30     Delete "salts" and substitute --salt--

Signed and Sealed this

Eighteenth Day of September 1984

[SEAL]

Attest:

GERALD J. MOSSINGHOFF

Attesting Officer     Commissioner of Patents and Trademarks